United States Patent [19]
Hayakawa et al.

[11] Patent Number: 5,837,721
[45] Date of Patent: Nov. 17, 1998

[54] THIFLUZAMIDE WITH STABILIZED EFFICACY

[75] Inventors: Norihito Hayakawa; Masatoshi Baba, both of Funabashi; Norihiro Suwa, Narashino; Kazuhiro Yamagishi, Tokyo, all of Japan

[73] Assignee: Rohm and Haas Company, Philadelphia, Pa.

[21] Appl. No.: 804,160

[22] Filed: Feb. 20, 1997

[51] Int. Cl.$^6$ .................. C07D 277/56; A01N 43/78
[52] U.S. Cl. .................................. 514/365; 548/200
[58] Field of Search .......................... 548/200; 514/365

[56] References Cited

U.S. PATENT DOCUMENTS 5,045,554  9/1991  Alt et al. .

OTHER PUBLICATIONS

Phillips, W.G. and Rejda–Heath, J.M., *Pesticide Science,* vol. 38, No. 1, 1993, pp. 1–7.

O'Reilly, P. et al, Brighton Corp Protection Conference—Pests and Diseases, No. 1, 1992, pp. 427–434.

*Primary Examiner*—Robert Gerstl
*Attorney, Agent, or Firm*—Thomas D. Rogerson

[57] ABSTRACT

The disclosed invention is thifluzamide with an altered crystalline form, prepared by heat-melting and then cooling, and agricultural chemical compositions comprising such a thifluzamide as its effective ingredient.

5 Claims, 2 Drawing Sheets

THIFLUZAMIDE WITH STABILIZED EFFICACY

This invention relates to N-(2,6-dibromo-4-trifluoromethoxyphenyl)-2-methyl-4-trifluoromethyl-5-thiazole carboxyamide (common name: thifluzamide) with an altered crystalline form, its preparation method, and agricultural chemical composition containing thifluzamide as its effective ingredient.

Figure 1:
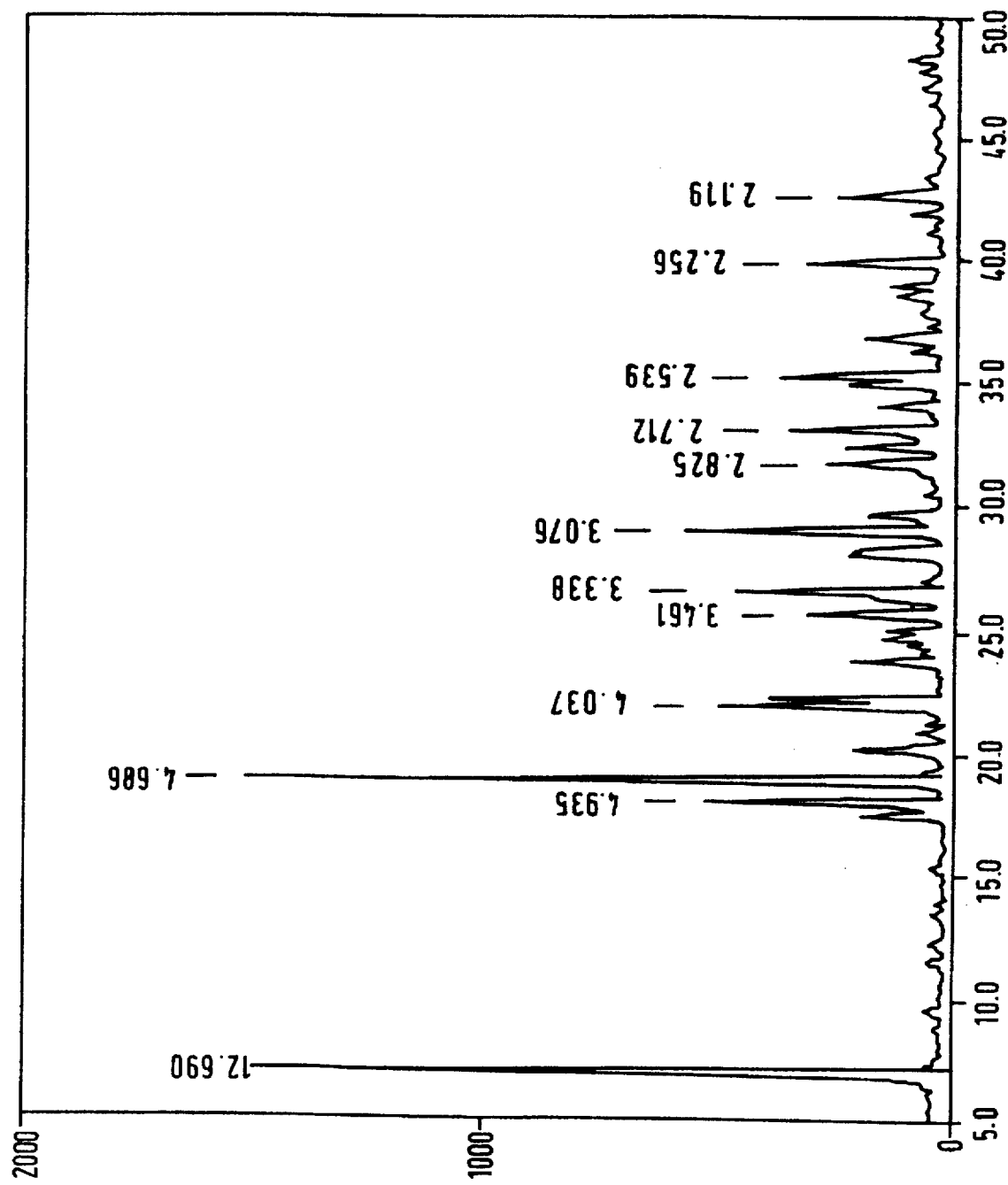
FIG. 1—Powder X-ray diffraction pattern of the α-crystalline thifluzamide obtained in the Reference Example.

Thifluzamide is a compound that has a high pesticidal activity against rice leaf spot withering disease. Because the time to use a chemical against rice leaf spot withering disease in the cultivation of rice plant is when the rice field is covered with a lesser amount of water, rate of release/diffusion of the effective ingredient affects the exterminating effect significantly. However, since water solubility of thifluzamide is extremely low, about 1.6 mg/l (20° C.), it is desirable to develop a method that can increase the rate of its release in water and stabilize its efficacy.

We have discovered that thifluzamide synthesized by ordinary preparation method changes its crystalline form when heat-melted and then cooled and that releasability of thifluzamide to water can be improved. As a result, the pesticidal efficacy can be stabilized by preparing an agricultural chemical composition using the thifluzamide with an altered crystalline form. Based on this discovery, the present invention was perfected.

Therefore, this invention is a process for preparing thifluzamide with an altered crystalline form, comprising heat-melting thifluzamide at a temperature above the melting point, preferably 180° C.–250° C., more preferably 180° C.–200° C. and then cooling to a temperature below the melting point.

Another embodiment of this invention is thifluzamide showing endothermic peak at 175°–180° C. by differential scanning calorimeter and having no other peak at less than that temperature.

A third embodiment of this invention is thifluzamide showing a peak at 2 θ=17.68, 20.04, 23.04, 28.88 and 29.52 by powder X-ray diffraction analysis.

A further embodiment of this invention is an agricultural chemical composition comprising thifluzamide with an altered crystalline form as an effective ingredient.

The melting point of thifluzamide is known to be 177.9°–178.6° C. (Pesticide Manual, 1994). However, the thifluzamide synthesized in the Reference Example to be stated later shows an endothermic peak in the vicinity of 178° C. by differential scanning calorimeter (DSC), and it shows an additional endothermic peak of 2.0–2.5 cal/g in the vicinity of 161° C. And, in powder X-ray diffraction analysis, it shows a diffraction pattern such like FIG. 1. In the following, thifluzamide of such crystalline form is called "α-crystal".

The thifluzamide of this invention with an altered crystalline form has a crystalline structure different from the α-crystal by powder X-ray diffraction analysis and DSC, as illustrated by the thifluzamide obtained in the Example 1 which will be stated later. Specifically, it shows an endothermic peak only in the vicinity of 178° C. by DSC and does not show an endothermic peak at less than that temperature. In powder X-ray diffraction analysis, it shows a diffraction pattern like FIG. 2 and shows a peak at 2θ=17.68, 20.04, 23.04, 28.88 and 29.52. In the following, thifluzamide having such crystalline form is called "β-crystal".

The β-crystalline thifluzamide of this invention is prepared by the following method. After heat-melting α-crystalline thifluzamide at a temperature higher than the normal melting point, preferably 180°–250° C., more preferably 180°–200° C., it is then cooled to lower than the melting point and recrystallized. Although the cooling rate is not critical, in this case, the cooling rate, in terms of the time required to crystallize from 190° C., is preferably 0.01 second–20 minutes, more preferably 0.01–20 seconds.

The β-crystalline thifluzamide of this invention can be prepared easily by transferring α-crystalline thifluzamide, which is molten at a temperature higher than its melting point, from a heating device such as a dryer to an environment that has a temperature lower than its melting point such as room temperature. It can also be prepared easily by adding dropwise or spraying the molten α-crystalline thifluzamide into a liquid such as water which is inert to thifluzamide and does not substantially dissolve the thifluzamide, or by spraying the thifluzamide into a gas such as air which is inert to the thifluzamide.

Even though there is no particular restriction about the form of the agent of the agricultural chemical composition of this invention wherein β-crystalline thifluzamide is used as the effective ingredient, powder, hydrates, pellets, tablets, granular hydrates, and suspension and so on can be mentioned as examples. Each of them can be prepared by ordinary methods known to those skilled in agricultural chemical formulation art. Furthermore, there is no particular restriction about the additives other than the β-crystalline thifluzamide to be added to the agricultural chemical composition of this invention. Also, other effective ingredients than β-crystalline thifluzamide may be added as the effective ingredients in the agricultural chemical composition of this invention.

We have discovered that the pesticidal efficacy and releasability of thifluzamide leaching into water from the agricultural chemical composition wherein the β-crystalline thifluzamide obtained in accord with this invention serves as the effective ingredient are improved, compared to when α-crystalline thifluzamide is used.

In addition to β-crystalline thifluzamide, the agricultural chemical composition of this invention includes also the situation where both α- and β-crystals of thifluzamides are used as a mixture, but the mixing ration of β-crystalline form is preferably 20–100%, more preferably 50–100%, from the viewpoint of improvement of solubility in water.

This invention is explained by the Reference Examples, Examples, and Examples of Tests illustrated below. However, this invention is not limited only to those examples. Incidentally, "parts" in the following Examples and Comparative Example means "parts by weight". And, DSC and powder X-ray diffraction analysis shown in the Reference Examples and Examples were run under the test conditions illustrated below.

DSC determination (in air)
Equipment DSC-3100, by Mac Science Co.
Weight of sample 3 mg
Sample pan Aluminum
Sampling rate 1.0 second Rate of temperature 5.0° C./minute elevation
Powder X-ray diffraction analysis
Equipment JDX-8200T, by Nippon Denshi K.K.
Target Cu 2θ=5°–50°
Step angle 0.04°
Counting time 0.5 second
Tube voltage 30.0 kV
Tube current 100.0 mA

REFERENCE EXAMPLE

Synthesis of α-crystalline Thifluzamide

2-Methyl-4-trifluoromethyl-5-chlorocarbonyl thiazole 6.47 g and 2,6-dibromo-4-trifluoromethoxy aniline 8.91 g were added in acetonitrile 16.8 ml, and they were heated to reflex for 6.5 hours. Solvent was removed from the reaction mixture by distillation under a reduced pressure, and then ethyl acetate 420 g and water 300 ml were added and they were agitated. After standing calmly, the ethyl acetate layer was collected, and washed with 300 ml each of water, saturated sodium bicarbonate solution, and water in succession. Then, after drying over anhydrous sodium sulfate, solvent was removed by distillation under a reduced pressure, to obtain thifluzamide 13.9 g.

The starting materials, 2-methyl-4-trifluoromethyl-5-chlorocarbonyl thiazole and 2,6-dibromo-4-trifluoromethoxy aniline, were synthesized by the procedures described in Example 1 of Japanese Kokai Patent No. 184680/1990.

The thus-obtained crystal showed an endothermic peak of 2.1 cal/g in the vicinity of 161° C. and another endothermic peak of 9.0 cal/g in the vicinity of 178° C. by DSC. And by powder X-ray diffraction analysis, as illustrated in FIG. 1, the relative peak intensity at 2θ=17.70 was I/Io=12, and at 2θ=23.0° was I/Io=11. The crystal obtained in this Reference Example was called a "α-crystal".

EXAMPLE 1

Synthesis of β-crystalline Thifluzamide

The α-crystalline thifluzamide 200 mg obtained in the Reference Example was placed in a glass Petri dish having a diameter of 3 cm. After the dish was placed in a dryer at 190° C. to melt the thifluzamide completely, it was taken out of the dryer, and then allowed to sit at room temperature to recrystallize. In this case, the time required by the thifluzamide taken out from the 190° C. dryer to crystallize completely was 20 seconds.

Figure 2:
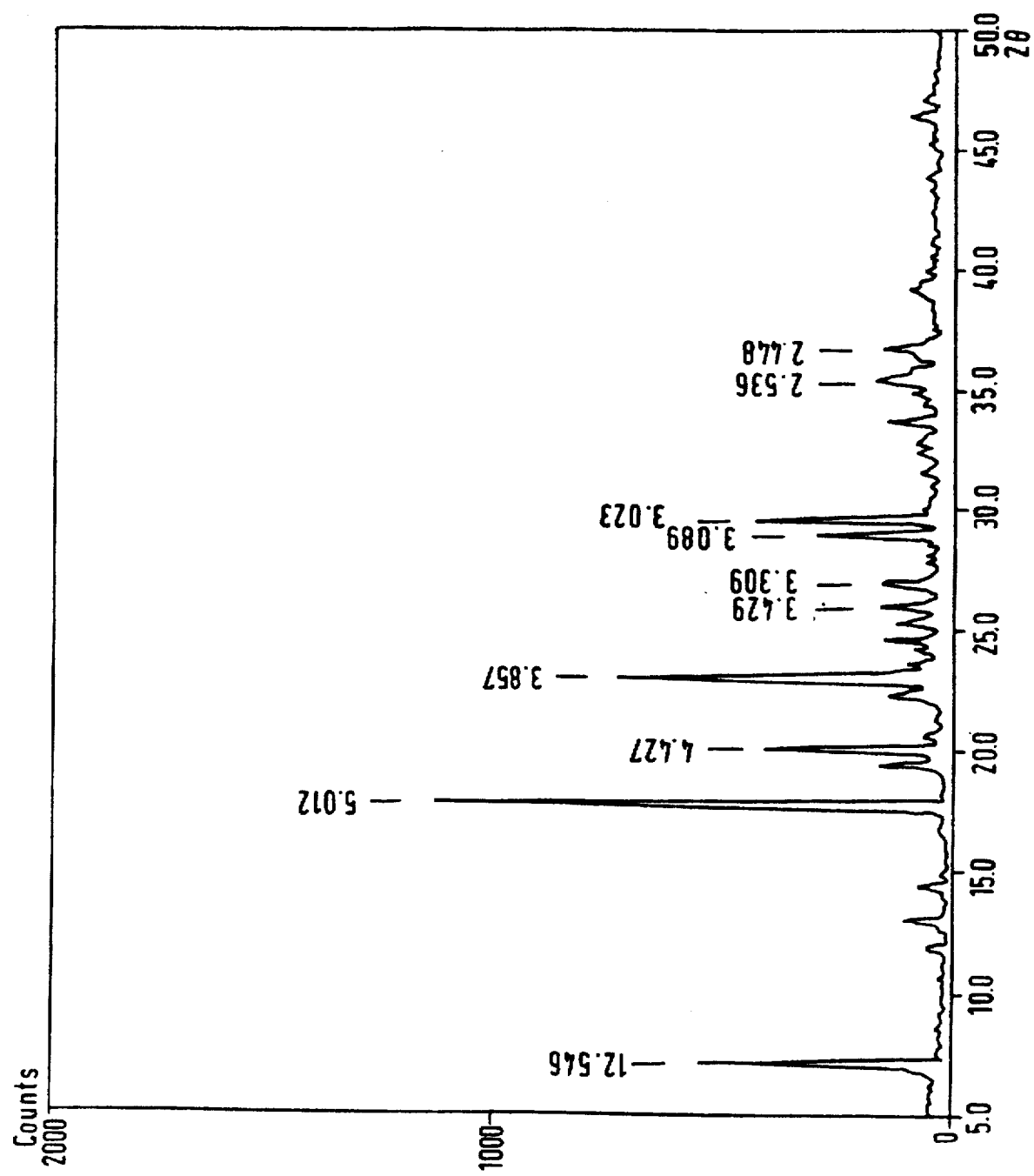
FIG. 2—Powder X-ray diffraction pattern of the β-crystalline thifluzamide obtained in the Example 1.

The thus-acquired crystal showed an endothermic peak of 9.5 cal/g in the vicinity of 178° C. by DSC, but it did not show a peak in the vicinity of 161° C. By powder X-ray diffraction analysis, as illustrated in FIG. 2, it showed a peak at 2θ=17.68, 20.04, 23.04, 28.88 and 29.52, and the relative peak intensity at 2θ=17.60 was I/Io=100 and the relative peak intensity at 2θ=23.0° was I/Io=59, and thus its crystalline form was different from that of α-crystal. The crystal obtained in this Example was called "β-crystal".

EXAMPLE 2

Pellet 1 (β-crystal)

The β-crystalline thifluzamide obtained in Example 1 was fractured by a jet crusher (A-0 Jet Mill, manufactured by Seishin Kigyo K.K.). This fractured material 2.0 parts, sodium lignin sulfonate 5.0 parts, alkylbenzene sulfonic acid 0.5 part, sodium polyacrylate 1.0 part, sodium tripolyphosphate 2.0 parts, bentonite 40 parts, calcium carbonate 49.5 parts, and water 16 parts were mixed and blended in an Almighty Mixer (manufactured by Dalton K.K.), and it was pelletized by using an extruder type pelletizer equipped with a screen having 0.8 mm apertures (BR-200, manufactured by Fuji Powdal K.K.). This pellet was dried at 50° C., to obtain a pellet 1 (β-crystal).

EXAMPLE 3

Pellet 2 (mixture of α+β crystals)

The thifluzamide (α-crystal) 35 parts obtained in the Reference Example and the thifluzamide (β-crystal) 65 parts obtained in the Example 1 were mixed/blended in a jet crusher (A-0 Jet Mill). This mixed/fractured thifluzamide showed an endothermic peak of 0.71 cal/g in the vicinity of 161° C. and another endothermic peak of 9.1 cal/g in the vicinity of 178° C. by DSC. And, the X-ray diffraction analysis confirmed that is was a mixture of α-crystal and β-crystal. This mixed/fractured thifluzamide (α-crystal: β-crystal=35:65) 2.0 parts was processed like Example 2, to obtain a pellet 2 (mixture of α+β crystals).

COMPARATIVE EXAMPLE

α-crystal

Procedure of Example 2 was applied on 2.0 parts of the jet-fractured thifluzamide (α-crystal) obtained in the Reference Example, to obtain a comparative pellet (α-crystal).

EXAMPLE OF TEST 1

Dissolution Test of Pellets

Forty five milligrams each of the pellets 1 and 2 and comparative pellet were added in a beaker containing hard water (hardness=10°) 1000 ml and kept at water temperature of 30° C. After standing calmly for 7 days, a portion of the solution was taken out from the center portion of the beaker, and content of thifluzamide was analyzed. Percent of thifluzamide being released was calculated by the following equation.

% Released=A×100/B

A: Amount (mg) of thifluzamide released to water

B: Content (mg) of thifluzamide in the pellet which was added to the beaker

Results are presented in Table 1.

EXAMPLE OF TEST 2

Test of Biological Effect

An are pot (1/10000 are size) containing the rice plants at its eighth leaf stage was treated with the pellet obtained in Example 2 and Comparative Example at a dose of 300 g/are. Seven days after the treatment, rice leaf spot withering pest (*Hydpochuns sasaki*) which was cultured ahead of time on rice hull media was wrapped in a cheese cloth and inserted between the stands of rice plants in the 1/10000 are pot to inoculate the pest.

After inoculation, the rice plants in the 1/10000 are pot were kept in a green house at 25° C. and a humidity of 100%. Seven days after inoculation, height of the highest spot reached by the pest to cause disease was measured from the spot of inoculation, and this was used to calculate the extermination value. Results are shown in Table 1.

TABLE 1

|  | Thifluzamide being released, on the 7th day (%) | Rice leaf spot withering disease extermination value, inoculated on the 7th day after treatment (%) |
| --- | --- | --- |
| Pellet 1 (β-crystal) | 100 | 80 |
| Pellet 2 (α + β crystals) | 80 | — |
| Comparative pellet (α-crystal) | 58 | 60 |

Rate of release of thifluzamide in water can be enhanced and efficacy as an agricultural chemical can be stabilized, by using the thifluzamide which has been converted into the crystalline form of this invention as the active ingredient of the agricultural chemical.

We claim:

1. A process for preparing β-crystalline thifluzamide, comprising the steps of:

a) heat-melting α-crystalline thifluzamide at a temperature above the melting point until molten and b) cooling the melted thifluzamide to a temperature below the melting point until recrystallized.

2. An agricultural chemical composition comprising β-crystalline thifluzamide prepared by the process of claim 1.

3. The process of claim 1 wherein the thifluzamide is heat-melted at a temperature of from 180° C. to 250° C.

4. The process of claim 1 wherein the thifluzamide is heat-melted at a temperature of from 180° C. to 200° C.

5. β-Crystalline thifluzamide prepared by the process of claim 1.

* * * * *